(12) United States Patent
Edmondson et al.

(10) Patent No.: US 6,384,249 B1
(45) Date of Patent: May 7, 2002

(54) COMPOUNDS AND METHODS FOR STABILIZATION OF FURFURAL COMPOSITIONS

(75) Inventors: James G. Edmondson, Conroe, TX (US); Grace B. Arhancet, Creve Coeur, MO (US)

(73) Assignee: Hercules, Inc., Wilmington, DE (US)

( * ) Notice: Subject to any disclaimer, the term of this patent is extended or adjusted under 35 U.S.C. 154(b) by 29 days.

(21) Appl. No.: 09/690,609

(22) Filed: Oct. 17, 2000

(51) Int. Cl.$^7$ ............................................. C07D 307/48
(52) U.S. Cl. ........................ 549/490; 549/483; 552/301; 508/184
(58) Field of Search ................................ 549/483, 490; 508/184; 552/301

(56) References Cited

U.S. PATENT DOCUMENTS

| | | |
|---|---|---|
| 5,332,842 A | 7/1994 | Dickakian |
| 5,453,519 A | 9/1995 | Dickakian |
| 5,470,440 A | 11/1995 | Arhancet |
| 5,562,863 A | 10/1996 | Arhancet |

FOREIGN PATENT DOCUMENTS

| | | |
|---|---|---|
| EP | 0467843 A2 | 1/1992 |
| EP | 0467844 A2 | 1/1992 |

*Primary Examiner*—T. A. Solola
(74) *Attorney, Agent, or Firm*—Hoffmann & Baron, LLP

(57) ABSTRACT

Inhibitor compounds containing a moiety according to this invention are used to inhibit air oxidation and thermal polymerization of furfural or furfural derivatives. A process is provided for use of the inhibitors in the solvent refining of lubricating oils where furfural is used to extract impurities including polycyclic aromatic and oxygen-containing compounds from the lubricating oils. The process provides for combination of the inhibitor with a continuously recirculating furfural stream in the extraction process.

17 Claims, 1 Drawing Sheet

Runs at 450°F

Inventive Inhibitor Compound Reduces Acidic Polymer Formation In Furfural Subject to Accelerated Oxidation at 450°F

COMPOUNDS AND METHODS FOR STABILIZATION OF FURFURAL COMPOSITIONS

FIELD OF THE INVENTION

The present invention relates generally to methods for preventing air oxidation and thermal polymerization of furfural or furfural derivatives by introduction of anti-oxidant compounds. More specifically, the present invention relates to the use of compounds containing specific moieties for preventing or decreasing the oxidation of furfural compositions.

BACKGROUND OF THE INVENTION

Furfural has many industrial applications. One of these includes its use to produce high quality petroleum lubricating oil by removing polycyclic aromatic compounds, sludges, and sulfur-, oxygen- and nitrogen-containing compounds. For example, polycyclic aromatic and oxygen compounds need to be removed from the lube oil fraction because they form polymers which plate out as varnish deposits on hot engine parts. The sulfur-, oxygen- and nitrogen-compounds in a lube oil fraction need to be removed because they can form acids which corrode types of alloys used in the manufacture of pumps and engines. Moreover, sludges must be removed from stocks of lube oil because they can reduce engine piston ring performance and may plug filters and oil lines. The impurities just described are removed from the lube oil feedstock by using furfural in a process referred to as furfural extraction.

In conventional processes using furfural extraction, the lube oil stock is mixed with the furfural in an extraction column. The lube oil/furfaral mixture is separated into two layers: one rich in furfural and containing the dissolved impurities (extract layer); the other rich in the desirable lube oil (raffinate layer). The main steps include: (a) extraction of the lube oil with furfural; (b) purification of the lube oil rich stream (raffinate); and (c) recovery of the furfural from the extract stream by a process which entails distillation after heating to about 450° F. under vacuum with steam stripping.

Problems associated with the use of furfural in the aforementioned extraction processes include its tendency to oxidize when exposed to atmospheric or dissolved oxygen, and to polymerize when heated to elevated temperatures, even in the absence of oxygen. These reactions result in the formation of undesirable oxidation products such as formic acid, formyl acrylic acid or furoic acid which can, upon heating, further produce acidic polymers. The acidic oxidation products and the acidic polymers can cause a number of problems, including the corrosion of metal extraction process equipment. Moreover, the deposition of corrosion by-products and of acidic polymers on equipment surfaces can lead to a number of operational problems, including restricting flow of fluids.

In general, it is extremely difficult to prevent air from coming into contact with furfural during its manufacture, storage and use. However, economics dictates that the furfural be recovered and recycled following use and, for that reason, efforts to reduce the undesired oxidation of furfural have included the use of a number of anti-oxidant compounds aimed at preventing or retarding the oxidation of furfural. For example, U.S. Pat. No. 4,045,332 discloses the use of dialkyl anilines for preventing degradation of furfural during the process of solvent extraction. European patent applications EP 467,843 A2 and EP 467,844 A2 disclose the use of hindered phenolic compounds and amine compounds, respectively, as anti-oxidant compounds for use in furfural. Japanese 60090 295 A also discloses the use of phenolic compounds as a corrosion inhibitor in furfural/oil mixtures.

Examples of commercially available phenols used as antioxidants for furfural include di-butyl methyl phenol (BHT) and di-nitro-para-cresol (DNPC). In general, these phenolic anti-oxidants have the disadvantage that they are ineffective at maintaining the acid number low enough for commercial acceptability. The acid number, determined by potentiometric titration of furfural, is a measure of the acid generated during air oxidation of furfural; when comparing the performance of inhibitors of furfural oxidation, those with the lowest acid numbers relative to an untreated sample are the most effective inhibitors.

U.S. Pat. No. 5,453,519 discloses the use of hindered amines such as phenylenediamines or naphthalendiamines and their substituted derivatives as inhibitors of the oxidation, degradation or polymerization of furfural and other furan compounds. In particular, the patent discloses a method for introducing into the furfural these compounds while maintaining the acidity of the furfural below a predetermined level by the addition of base. While phenylenediamines are alleged to be more effective at reducing acid formation during oxidation of furfural when compared with phenolic antioxidants, undesirable acidic polymers still may be generated even in the presence of such phenylenediamines. As described above, these polymers can cause fouling of equipment surfaces and restricted flow rates.

It would therefore be desirable to provide for other anti-oxidant compounds and compositions which can effectively reduce the acid number of furfural so as to significantly reduce its oxidation and degradation, while decreasing the formation of acidic polymers as compared to current methods and compositions.

SUMMARY OF THE INVENTION

Figure 1:
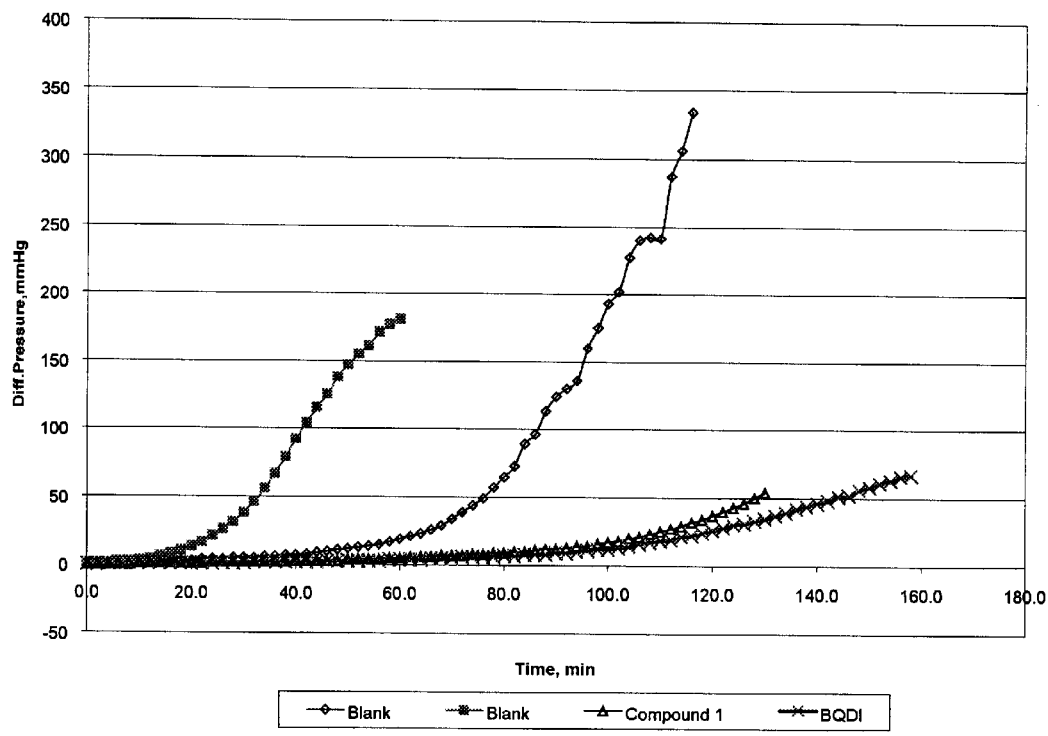
FIG. 1 is a graph depicting the differential pressure across a filter versus time for experimental runs at 450° F. using a test heat exchanger device.

The method of the present invention includes the use of highly conjugated inhibitors and their substitute derivatives as anti-oxidants in furfural or furfural derivatives. In particular, a process is disclosed for inhibiting oxidation of furfural, which process includes combining furfural or a composition containing furfural with an effective amount of an inhibitor compound containing a moiety having the following formula:

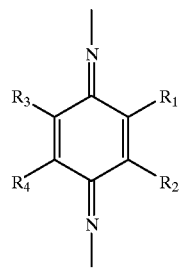

wherein R1, R2, R3 and R4 are independently hydrogen or $C_{1-8}$ alkyl, substituted or unsubstituted, linear or branched. The anti-oxidant is used in quantities sufficient to inhibit the oxidation and/or polymerization of the furfural or furfural derivatives. One most desirable inhibitor compound contains the aforementioned moiety wherein R1, R2, R3 and R4 are each hydrogen.

A further process is disclosed for inhibiting oxidation of furfural during solvent refining of lubricating oils, wherein this process includes introducing into a continuously circulating furfural stream an effective amount of an inhibitor compound containing a moiety having the following formula:

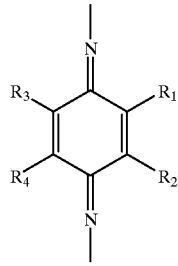

wherein R1, R2, R3 and R4 are independently hydrogen or $C_{1-8}$ alkyl, substituted or unsubstituted, linear or branched.

DETAILED WRITTEN DESCRIPTION

As indicated above, the present invention involves a process for reducing the oxidation, degradation or polymerization of furfural and other furan compounds. Since furfural is unstable in the presence of oxygen especially at elevated temperatures, its use as an extractant for lube oil is practical only if oxygen is rigorously excluded. This is very difficult to do in practice and, therefore treatment with stabilization compounds makes its use commercially viable. The present invention provides stabilization compounds for furfural and its derivatives which include the aforementioned moites.

The processes of the present invention are specifically directed to the treatment of furfural and furan compounds that have a tendency to oxidize or polymerize in the presence of atmospheric or dissolved oxygen. While the present invention will be described specifically with reference to furfural, the invention is intended to have application with derivatives of furfural, including without limitation furan, furfural alcohol, tetrahydrofurfural and tetrahydrofuran acid. In general, these compounds are characterized by a doubly unsaturated five-membered hetero ring of four carbon atoms and one oxygen atom.

The present invention describes the use of compounds as inhibitors of the oxidation of furfural during either the manufacture, storage or use of furfural. The inhibitors useful in the processes of the present invention contain a moiety having the following formula:

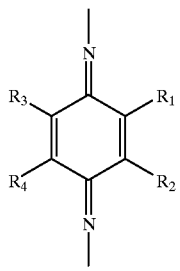

wherein R1, R2, R3 and R4 are independently hydrogen or $C_{1-8}$ alkyl, substituted or unsubstituted, linear or branched. Desirable inhibitors are those wherein R1, R2, R3 and R4 are each hydrogen.

A desired inhibitor compound containing the moiety of this invention for combination with furfural or a composition containing furfural, has the following formula:

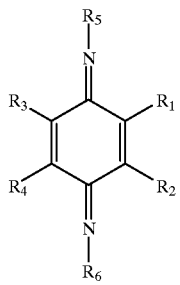

wherein R1, R2, R3, and R4 may be independently hydrogen or $C_{1-8}$ alkyl, substituted or unsubstituted, linear or branched; and R5 and R6 may be independently hydrogen, $C_{1-20}$ alkyl, cycloalkyl, alkenyl, aryl, alkaryl, aralkyl, substituted or unsubstituted, linear or branched.

In one aspect of the present invention, there is included a process for treating the furfural with an anti-oxidant compound which includes the combination of furfural or a composition containing furfural with an inhibitor compound having the following formula:

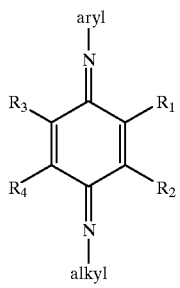

wherein aryl may be a phenyl, an alkylated phenyl, or naphthyl group and alkyl is $C_{1-20}$ alkyl, substituted or unsubstituted, linear or branched; and R1, R2, R3 and R4 may be independently hydrogen or $C_{1-8}$ alkyl, substituted or unsubstituted, linear or branched.

In one embodiment, the aryl group is a phenyl or alkylated phenyl group. In yet another embodiment, the alkyl group, which may be substituted or unsubstituted, straight or branched is a $C_{1-8}$ alkyl group.

A specific inhibitor useable in the method of the present invention is benzamine, N-[4-[(1,3-dimethyl butyl) imino]-2,5-cyclohexadien-1-ylidine, a compound referred to here as a benzoquinonediimide (BQDI). In this compound, the two keto oxygens normally present on quinones have been replaced with imine nitrogens With specific reference to the furfural compound, the inhibitor of this invention is present in the furfural composition at a concentration of about 5 to about 1,000 ppm. Preferably, the inhibitor of the present invention is present in the furfural composition at a concentration of about 5 to about 100 ppm.

While the inhibitor may be used in a substantially pure form, it can also be used in a composition which would include other compounds such as dispersants, solvents, or other anti-oxidants. Other anti-oxidant compounds can include phenolic anti-oxidants, as well as phenylenediamines. Dispersants include those useful for dispersing organic compounds, such as lube oil dispersants. An example of a useful dispersant is PIBSA-PAM (polyisobutylene succinic anhydride reacted with either a polyamine as described in U.S. Pat. No. 3,804,765 or a polyethylene amine).

The process of combining furfural or its derivatives with an inhibitor according to this invention, may further include maintaining the acidity of the furfural or its derivatives at about a neutral pH by the addition of a base. Suitable bases may include solid alkali bases as well as liquid amines. Desirable bases include low molecular weight liquid amines and hydroxy amines. Non-limiting examples of such bases include ethyl-and triethyl amines, diethyl diamines, propyl amine, hydroxyl amine, triethanolamine, diethyl triamine, ethylene diamine, and morpholine, among others. Moreover, combinations of bases may be useful.

When excessive oxygen is present in the furfural, maintaining the acidity of the furfural at about a neutral pH is particularly important. For example, the generation of acidic polymeric by-products is dependant on the initial acidic product formation. Generally speaking, a higher acid content results in greater amounts of polymers being formed because the presence of acids catalyzes polymerization as well as the production of polymeric by-products. As discussed above, the generation of acidic polymers leads to corrosion of metal equipment surfaces and equipment fouling. Neutralization treatment can be accomplished by adjusting the acidity of the furfural to about neutral pH by the addition of a suitable base such as a liquid amine. Introduction of the inhibitor into the furfural can take place while continuing to maintain the acidity of the furfural at a level of about neutral pH.

Deposition of acidic polymers on equipment, which leads to restricted flow of fluids and corrosion, is particularly problematic at the acidities typically encountered in the furfural extraction process used in the purification of lubricating oils, where oxygen contamination is prevalent. Therefore, the present invention provides for a process for inhibiting the oxidation of furfural during solvent refining of lubricating oils as a means to prevent or reduce equipment fouling and corrosion. This process includes introducing into a continuously circulating furfural stream an effective amount of an inhibitor compound containing a moiety having the following formula:

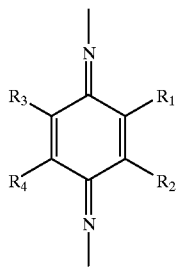

wherein R1, R2, R3 and R4 are independently hydrogen or $C_{1-8}$ alkyl, substituted or unsubstituted, linear or branched.

In one embodiment, the inhibitor compound introduced into the circulating furfural stream has the following formula:

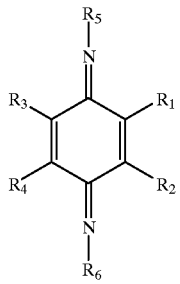

wherein R1, R2, R3 and R4 are independently hydrogen or $C_{1-8}$ alkyl, substituted or unsubstituted, linear or branched; and R5 and R6 are independently hydrogen, $C_{1-20}$ alkyl, cycloalkyl, alkenyl, aryl, alkaryl, aralkyl, substituted or unsubstituted, linear or branched.

Particularly useful inhibitor compounds in the method of the present invention have the following formula:

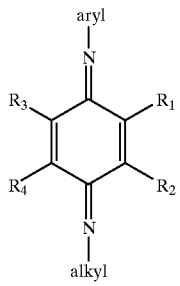

wherein aryl is a phenyl, an alkylated phenyl, or naphthyl group and alkyl is a $C_{1-20}$ alkyl, substituted or unsubstituted, linear or branched; and R1, R2, R3, and R4 are independently hydrogen or $C_{1-8}$ s alkyl, substituted or unsubstituted, linear or branched. The aryl group is preferably a phenyl or alkylated phenyl group. Furthermore, the alkyl group is preferred to be a $C_{1-8}$ alkyl group.

Because of the severity of furfural oxidation which occurs during furfural solvent extraction of lubricating oils, the acid levels generated may require that the process of the present invention include maintaining the acidity of the furfural stream at about a neutral pH by the addition of a suitable base such as those previously described. In addition to adding the neutralizing base prior to the combination of the inhibitor with the furfural stream, the process of the present invention may further include the periodic neutralization to adjust and/or maintain the acidity to about a neutral pH. The monitoring of the acid level can be achieved by potentiometric titration. The amount of neutralizer in the system will depend on the degree of adjustment, but concentrations of 10 to 200 ppm of the base in the furfural has been found to be sufficient.

In a particularly desirable embodiment, the inhibitor compound of the present invention is introduced into the furfural stream at a concentration of about 5 to about 1,000 ppm, and desirably at about 5 to about 100 ppm based on the amount of furfural composition present.

The inhibitor and base may be injected into the system at the same location. Because the portions of the furfural extraction process most susceptible to furfural acid corrosion (oxygen-generated) include the furfural feed tank and lines, and all exchangers, pumps, towers, furnaces, and settling drums in the extract circuit, it is desired that the inhibitor be fed to the furfural storage tank or as far upstream of the affected equipment as possible. For example, in the refining of lubricating oils by solvent extraction, the furfural is brought into contact with a lubricating oil in a counter-flow extraction tower from a furfural feed tank. The furfural extracts the impurities from the lube oil and exits the bottom of the tower. The furfural stream is then recovered, purified and recycled to the lube oil furfural counter-flow extraction tower. It is preferred that the inhibitor of the present invention is introduced into the furfural stream upstream of the lube oil furfural counter-flow extraction tower.

In addition to corrosion, the fouling of feedlines and heat exchangers in a furfural extraction unit caused by the polymerization of the furfural or lube oil stock in each feedline, is another reason why it is desirable that the inhibitor be fed to the furfural storage tank or as far upstream of the lube oil furfural counter-flow extraction tower as possible.

EXAMPLES

Example 1

Example 1 is intended to demonstrate the effectiveness of an inhibitor compound of the present invention at inhibiting acid generated during air oxidation of furfural. In this example, the inventive compound benzamine, N-[4-[(1,3-dimethyl butyl) imino]-2,5-cyclohexadien-1-ylidine, which is a benzoquinonediimide (BQDI), was evaluated against the following prior art compounds: (a) Compound #1, a dialkylphenylenediamine disclosed in U.S. Pat. No. 5,453,519 and sold under the trade name Hitec 4720 by Ethyl Corporation, Richmond, Va.; (b) Compound #2, an I-3, alkylarylphenylenediamine sold under the trade name Naugard I-3 by Uniroyal Chemical Company, Inc., Middlebury, Conn.; and (c) Compound #3, a butylated hydroxytolulene (BHT) which is 2,6-di-tert-butyl-4-methylphenol, disclosed in EP 0467843 A2; The structures of these compounds are shown below:

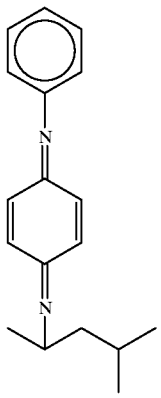

BQDI

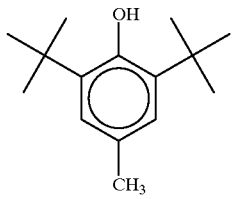

Compound #3 (Prior Art)

Compound #1 (Prior Art)

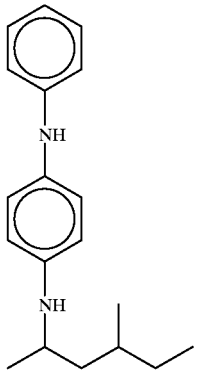

Compound #2 (Prior Art)

In this example, distilled furfural was treated with prospective stabilizers, over-pressured with 25 psig of air, heated to 300° F., and held at temperature for 2 hours to allow for an accelerated rate of furfural oxidation. Total Acid Number (TAN) titrations were then conducted by potentiometric titration on the treated furfural samples, an untreated (blank), and a sample of the original distilled material (control), which was not heated to 300° F. The acid number, expressed as mg KOH/g, is a measure of the acid generated during air oxidation of furfural. Performance of inhibitors was expressed as a percent inhibition by the following equation:

$$\%\text{Inhibition} = 100 * (TAN_{treated} - TAN_{blank})/(TAN_{blank} - TAN_{control}).$$

Results of these tests are tabulated below.
  Compound #1 (prior art): dialkylphenylenediamine (Hitec 4720)
  Compound #2: (prior art) an I-3, alkylarylphenylenediamine (Naugard I-3)
  Compound #3 (prior art): butylatedhydroxytolulene (BHT)
  Compound #4 (Inventive inhibitor): FlexSys Q-Flex QDI, alkylarylquinonediimide (BQDI)

|  | % Inhibition @ ppmA* | | | | TAN mg KOH/g | |
| --- | --- | --- | --- | --- | --- | --- |
| Compound | 250 | 500 | 1000 | 2000 | Blank | Control |
| #1 | — | 106 | 88 | 57 | 0.91 | 0.56 |
| #1 | 69 | 114 | 170 | — | 2.45 | 1.90 |
| #2 | 15 | 37 | 56 | — | 0.82 | 0.36 |
| #3 | −10 | −5 | 12 | — | 1.40 | 0.81 |
| #4 | 48 | 76 | 95 | — | 3.51 | 2.76 |

*The concentrations of the stabilizer compoumds shown im the table are the amount of the active ingredient of the stabilizer by weight per weight of the furfural composition.

These results demonstrate that when the inhibitor BQDI of this invention is present at a concentration of 1000 ppm, there is a 95% inhibition in the amount of acid generated, as compared to an untreated sample. This percent inhibition is comparable to that obtained with prior art Compound #1 at 1000 ppm which was determined to be 88% inhibition in one run and 170% in a second run, which based on the other results for this compound appears to be an experimental error. A phenolic prior art compound, BHT, gave only a 12% inhibition of the amount of acid generated compared with the untreated sample at 1000 ppm, while Compound #2 gave a 56% inhibition of the acid generated when used at 1000 ppm.

When used at a 500 ppm concentration, the inventive compound BQDI showed a 76% inhibition as compared with an untreated sample.

This test is not a good predictor of useful field dosages of the inventive compound due to the high oxygen content and high initial acid concentration in the furfural composition. In practice, useful concentrations of the inventive inhibitor compound are in the range of about 5 to about 100 ppm by weight per weight of the furfural composition.

Example 2

While Example 1 demonstrates that both the inventive compound BQDI and prior art Compound #1 are about equal in their ability to reduce the acid generated during air oxidation of furfural at 1,000 ppm concentration, Example 2 demonstrates that the inventive compound is superior to Compound #1 in its ability to reduce the amount of acidic polymer formation during furfural oxidation. Since fouling of feed lines and heat exchangers is a significant problem encountered in a furfural extraction unit, any meaningful reduction in the fouling caused by acidic polymer formation is beneficial.

In Example 2, BQDI, an inhibitor compound according to the present invention, was evaluated against prior art Compound #1 and a blank (untreated). For this example, the test method for evaluating acid generated involved the use of a commercial test heat exchanger device known as a "Hot Process Liquid Simulator" or HLPS. In this device, a fluid is drawn from a reservoir and electrically heated. In these experiments, the fluid was a synthetic extract mixture made from a vacuum distillate (from a Gulf Coast lube plant) and distilled furfural. The two liquids were mixed at a 2115:1000 ratio for 66 minutes at 180° F. and the furfural layer was withdrawn for HLPS testing (Extract Mixture or EM). The temperature of the EM exiting the heat exchanger was controlled at 450 or 500° F. At these elevated temperatures, an accelerated rate of furfural oxidation occurs. For the runs at 450° F., shown in the graph in FIG. 1 below, the differential pressure across a filter placed in the outlet stream was recorded versus time. Upon heating, the EM degrades and generates insoluble products which are trapped on the filter. In general, as more insoluble acidic polymers are trapped on the filter, the differential pressure across the filter increases. The time at which the differential pressure increases sharply is a measure of the relative stability of the EM. The inventive compound was tested relative to Compound #1, each at 24 ppmA. The results at 450° F. in FIG. 1 demonstrate that the inventive compound BQDI is more effective than Compound #1 at reducing the differential pressure across the filter following 100 min. This shows that there is less formulation and build-up of the acidic polymers on the filter when furfural is treated with the inventive compound as compared with prior art Compound #1. This is further demonstrated by results obtained at 500° F., which are shown in the table below. At 500° F., the rate of oxidation and degradation of furfaral would be even more increased relative to the degradation/oxidation rate at 450° F., such that insoluble degradation products such as acidic polymers are formed at and adhere to a rod. For these experiments at 500° F., the rod was weighed before and after the test to determine the degree of fouling. The results in the table below show that the inventive compound BQDI is four times more effective than prior art Compound #1 at reducing the amount of acidic polymers generated when furfural is oxidized at the elevated temperatures conventionally used during the furfural extraction process and during the process of distilling furfural for recycling. This should provide a significant improvement in the ability to operate extraction process equipment without shut-downs due to fouling of the equipment.

Runs at 500° F.

| Rod Deposits @ 500° F. | |
| --- | --- |
| Treatment | Deposit Weight, mg |
| Blank | 10 |
| Compound #1 | 0.4 |
| BQDI | 0.1 |

Runs at 450° F.

What is claimed:
1. A process for inhibiting oxidation of furfural, which process comprises combining a composition comprising furfural with an effective amount of an inhibitor compound of the following formula:

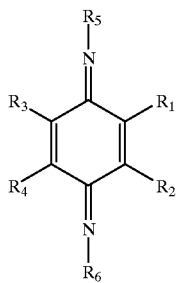

wherein $R_1$, $R_2$, $R_3$ and $R_4$ are independently hydrogen or $C_{1-8}$ alkyl, substituted or unsubstituted, linear or branched $R_5$ and $R_6$ are independently H or a saturated or unsaturated substituted or unsubstituted alkyl or aryl group.

2. A process according to claim 1 wherein the inhibitor compound has the following formula:

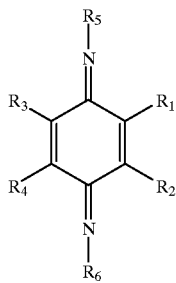

wherein $R_1$, $R_2$, $R_3$ and $R_4$ are independently hydrogen or $C_{1-8}$ alkyl, substituted or unsubstituted, linear or branched; $R_5$ and $R_6$ are independently hydrogen, $C_{1-20}$ alkyl, cycloalkyl, alkenyl, aryl, alkaryl, aralkyl, substituted or unsubstituted, linear or branched.

3. The process according to claim 1 wherein the inhibitor compound has the following formula:

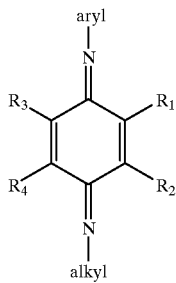

wherein aryl is a phenyl, alkylated phenyl, or naphthyl group and alkyl is $C_{1-20}$ alkyl, substituted or unsubstituted, linear or branched; $R_1$, $R_2$, $R_3$ and $R_4$ are independently hydrogen or $C_{1-8}$ alkyl, substituted or unsubstituted, linear or branched.

4. The process according to claim 3 wherein the aryl group is a phenyl or alkylated phenyl group.

5. The process according to claim 3 wherein the alkyl group is a $C_{1-8}$ alkyl group.

6. The process according to claim 1 further comprising maintaining the acidity of the furfural at about a neutral pH by the addition of a base.

7. The process according to claim 1 wherein the inhibitor compound is present in the furfural at a concentration of about 5 to about 1000 ppm.

8. The process according to claim 1 wherein the inhibitor compound is present in the furfural at a concentration of about 5 to about 100 ppm.

9. A process for inhibiting oxidation of furfural during solvent refining of lubricating oils, said process comprising introducing into a continuously circulating furfural stream an effective amount of an inhibitor compound of the formula:

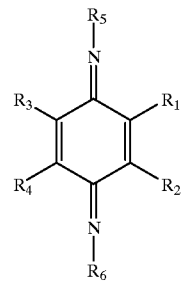

wherein $R_1$, $R_2$, $R_3$ and $R_4$ are independently hydrogen or $C_{1-8}$ alkyl, substituted or unsubstituted, linear or branched, $R_5$ and $R_6$ are independently H or saturated or unsaturated, substituted or unsubstituted alkyl or aryl group.

10. The process according to claim 9 wherein the inhibitor compound has the following formula:

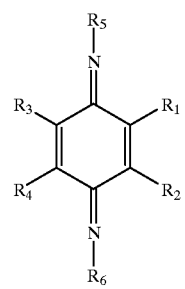

wherein $R_1$, $R_2$ $R_3$ and $R_4$ are independently hydrogen or $C_{1-8}$ alkyl, substituted or unsubstituted, linear or branched; $R_5$ and $R_6$ are independently hydrogen, $C_{1-20}$ alkyl, cycloalkyl, alkenyl, aryl, alkaryl, aralkyl, substituted or unsubstituted, linear or branched.

11. The process according to claim 9 wherein the inhibitor compound has the following formula:

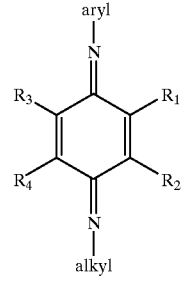

wherein aryl is a phenyl, alkylated phenyl, or naphthyl group and alkyl is $C_{1-20}$ alkyl, substituted or unsubstituted, linear or branched; $R_1$, $R_2$, $R_3$ and $R_4$ are independently hydrogen or $C_{1-8}$ alkyl, substituted or unsubstituted, linear or branched.

12. The process according to claim 9 wherein the inhibitor is introduced into the furfural stream upstream of the lube oil furfural counter-flow extraction tower.

13. The process according to claim 9 further comprising maintaining the acidity of the furfural stream at about a neutral pH by the addition of base.

14. The process according to claim 9 wherein the inhibitor compound is present at a concentration of about 5 to about 1000 ppm.

15. The process according to claim 9 wherein the inhibitor compound is present at a concentration of about 5 to about 100 ppm.

16. The process according to claim 11 wherein the aryl group is a phenyl or alkylated phenyl group.

17. The process according to claim 11 wherein the alkyl group is a $C_{1-8}$ alkyl group.

* * * * *